United States Patent [19]
Lipshitz et al.

[11] Patent Number: 5,876,442
[45] Date of Patent: Mar. 2, 1999

[54] INTRAOCULAR LENS IMPLANT WITH TELESCOPE SUPPORT

[75] Inventors: Isaac Lipshitz, Herzelia Pituach; Yosef Gross, Moshav Mazor; Gideon Dotan, Yehud, all of Israel

[73] Assignee: Visioncare Ltd., Yehud, Israel

[21] Appl. No.: 7,379

[22] Filed: Jan. 15, 1998

[51] Int. Cl.⁶ .................................................. A61F 2/16
[52] U.S. Cl. .................................................. 623/6
[58] Field of Search .................................................. 623/6

[56] References Cited

U.S. PATENT DOCUMENTS

| | | | |
|---|---|---|---|
| 4,074,368 | 2/1978 | Levy, Jr. et al. | 623/6 |
| 4,172,297 | 10/1979 | Schlegel . | |
| 4,731,078 | 3/1988 | Stoy et al. | 623/6 |
| 4,759,761 | 7/1988 | Portnoy | 623/6 |
| 4,863,468 | 9/1989 | Feinbloom et al. | 623/6 |
| 5,275,623 | 1/1994 | Sarfarazi | 623/6 |
| 5,354,335 | 10/1994 | Lipshitz et al. | 623/6 |
| 5,391,202 | 2/1995 | Lipshitz et al. | 623/6 |

FOREIGN PATENT DOCUMENTS

| | | |
|---|---|---|
| 0 212 616 | 3/1987 | European Pat. Off. . |
| 2666735 | 3/1992 | France . |

*Primary Examiner*—Mary Beth Jones
*Attorney, Agent, or Firm*—Darby & Darby

[57] ABSTRACT

An intraocular lens (IOL) implant for implantation in an eye having a capsular bag, a posterior chamber and an anterior chamber, the implant including a first carrying member adapted to be attached to the capsular bag, and a telescope attached to and extending from the first carrying member, characterized by the telescope being further attached to at least one second carrying member, wherein the at least one second carrying member is adapted to be attached to a portion of the eye.

15 Claims, 2 Drawing Sheets

INTRAOCULAR LENS IMPLANT WITH TELESCOPE SUPPORT

FIELD OF THE INVENTION

The present invention relates generally to intraocular lens (IOL) implants and particularly to an intraocular lens implant with a telescope support.

BACKGROUND OF THE INVENTION

Intraocular inserts comprising telescopes are known. European Published Patent Application EP-A-212616 describes an intraocular lens that includes an anterior convex lens and a posterior concave lens. The contour of the lens can be selectively changed by varying the amount of fluid therein in order to change its refractive power. The lens is intended solely as a replacement for the natural lens of the eye.

U.S. Pat. No. 4,074,368 also describes an intraocular lens that includes an anterior convex lens and a posterior concave lens with high magnification proposed for the relief of conditions such as macular degeneration and diabetic retinopathy. The lens has many relatively low power lens surfaces arranged in a relatively long lens assembly which extends, when implanted, through almost the entire depth of the eye, from the pupil nearly to the retina. Implanting such a lens would necessitate major surgery. Moreover, the proposed lens does not provide a replacement for the natural lens for a wide field of view.

French Published Patent Application 2,666,735 describes an implant that includes a lens-shaped optical portion and a fastening assembly for securing the implant in the eye. The optical portion includes at least one closed internal cavity which contains a fluid or vacuum, forming a refraction chamber changing the optical properties of the lens.

Applicant/assignee's U.S. Pat. Nos. 5,354,335 and 5,391,202, the disclosures of which are incorporated herein by reference, describe intraocular inserts with a positive (converging) lens facing the anterior side of the eye and a negative (diverging) lens facing the posterior side, the two lenses forming a Galilean telescopic system. In U.S. Pat. No. 5,354,335, the lenses are assembled in a body member, the positive lens being generally flush with the anterior face of the body member. The negative lens may either be flush with the posterior face of the body member, or may project posteriorly therefrom. The body member anterior and/or posterior faces may be convex. In U.S. Pat. No. 5,391,202, the positive lens projects anteriorly from the anterior face of the body member which is preferably a soft lens constructed from a material such as a silicone.

In U.S. patent application Ser. No. 08/882,972, the disclosure of which is incorporated herein by reference, the present applicant/assignee discloses a further intraocular implant comprising a telescope body having an anterior end and a posterior end and including one or more windows sealed to the telescope body at the anterior end and/or the posterior end. There are at least two lenses disposed within the telescope body intermediate the anterior and posterior ends. The lenses may be a so-called reverse Galilean telescope, i.e., a negative lens faces the anterior side of the eye while a positive lens faces the posterior side of the eye. One of the features of the system is that the lenses are doublet lenses. The windows may be formed without optical power, or alternatively, may comprise a prism.

In U.S. patent application Ser. No. 08/882,973, the disclosure of which is incorporated herein by reference, the present applicant/assignee discloses yet another intraocular implant comprising a telescope (either Galilean or reverse Galilean) which extends through at least a portion of a lens capsule of the eye and forwardly thereof toward the anterior side of the eye, the telescope not penetrating the vitreous of the eye. The intraocular lens implant is supported within the lens capsule by loops, in the absence of a lens within the lens capsule. One of the features of the system is that the telescope may be tilted such that light from outside the eye is focused by the telescope on a low resolution but operative section of the retina. Other optional features of the system include one or more lenses having a graded index of refraction, holographic (diffusing) lenses, and/or doublet lenses which help prevent chromatic aberrations. The patent application also discloses a method for manufacturing an intraocular insert telescope employing laser fusing to join the lenses to the telescope body. Alternatively or additionally, the method employs glass particles having a low temperature melting point as a joining medium.

SUMMARY OF THE INVENTION

The present invention seeks to provide an improved telescopic lens system extending from an IOL. In the present invention, a telescope body is supported by at least two carrying members placed at opposite ends of the telescope or at any other arbitrary positions along the telescope body. By supporting the telescope by more than one carrying member, any vibration or undesired displacement of the telescope is reduced or eliminated.

The term "carrying member" as used in the specification and claims is to be understood as any structure suitable for implantation in the eye and which is used to support the telescope in the eye. The carrying member of the present invention may or may not be a lens.

There is thus provided in accordance with a preferred embodiment of the present invention an intraocular lens (IOL) implant for implantation in an eye having a capsular bag, a posterior chamber and an anterior chamber, the implant including a first carrying member adapted to be attached to the capsular bag, and a telescope attached to and extending from the first carrying member, characterized by the telescope being further attached to at least one second carrying member, wherein the at least one second carrying member is adapted to be attached to a portion of the eye.

In accordance with a preferred embodiment of the present invention the first carrying member is attached to an end of the telescope and the at least one second carrying member is attached to an opposite end of the telescope. Alternatively the first carrying member is attached to an end of the telescope and the at least one second carrying member is attached to the telescope intermediate the end and an opposite end of the telescope.

Further in accordance with a preferred embodiment of the present invention the at least one second carrying member is adapted to be attached to a portion of the posterior chamber.

In accordance with an alternatively preferred embodiment of the present invention the telescope is adapted to extend through at least a portion of the capsular bag into the anterior chamber and the at least one second carrying member is adapted to be attached to a portion of the anterior chamber.

Preferably the first and the at least one second carrying members each include at least one haptic extending therefrom for attachment to a portion of the eye.

In accordance with a preferred embodiment of the present invention the first and the at least one second carrying members each have a bore formed therein and wherein the telescope is fixedly received in the bores. Preferably the bores are Generally circular. Preferably a center of each bore is generally concentric with a center of the corresponding carrying member. Alternatively, the center of at least one of the bores is offset from the center of the corresponding carrying member.

Additionally in accordance with a preferred embodiment of the present invention the telescope includes an anteriorly positioned positive lens and a posteriorly positioned negative lens.

Alternatively in accordance with another preferred embodiment of the present invention the telescope includes an anteriorly positioned negative lens and a posteriorly positioned positive lens.

Further in accordance with a preferred embodiment of the present invention the telescope includes lenses having a graded index of refraction.

Still further in accordance with a preferred embodiment of the present invention the telescope includes at least one holographic lens. The telescope may include at least one doublet lens.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
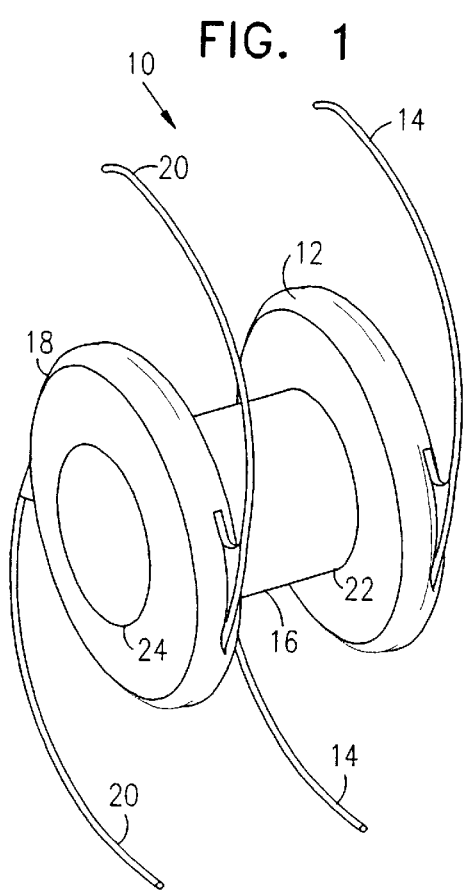
FIG. 1 is a simplified pictorial illustration of an intraocular lens implant comprising a first carrying member attached to an end of a telescope and a second carrying member attached to an opposite end of the telescope, constructed and operative in accordance with a preferred embodiment of the present invention.

Reference is now made to FIG. 1 which illustrates an intraocular lens implant 10 constructed and operative in accordance with a preferred embodiment of the present invention.

Implant 10 includes a first carrying member 12 adapted to be attached to a capsular bag (as will be shown in FIGS. 3 and 4), such as by means of one or more haptics 14 extending from the body of first carrying member 12. First carrying member 12 is attached to an end of a telescope 16, which telescope may be a Galilean or reverse Galilean telescope, as described further hereinbelow. At least one second carrying member 18 is attached to an opposite end of telescope 16, second carrying member 18 being adapted to be attached to a portion of an eye, (as will also be shown in FIGS. 3 and 4), such as by means of one or more haptics 20 extending from the body of second carrying member 18.

Carrying members 12 and 18 may be constructed of any material suitable for IOL's, such as polymethylmethacrylate (PMMA), glass, sapphire or the like. Carrying members 12 and 18 may be joined to the body of telescope 16 by any suitable method, such as by laser fusing in accordance with the teachings of the abovementioned U.S. patent application Ser. No. 08/882,973, for example. Preferably carrying members 12 and 18 have bores 22 and 24, respectively, formed therein, telescope 16 being fixedly received in these bores. Most preferably bores 22 and 24 are generally circular. In accordance with one embodiment of the present invention, as shown in FIG. 1, bores 22 and 24 are generally concentric with a center of the corresponding carrying member 12 or 18, respectively.

Figure 3:
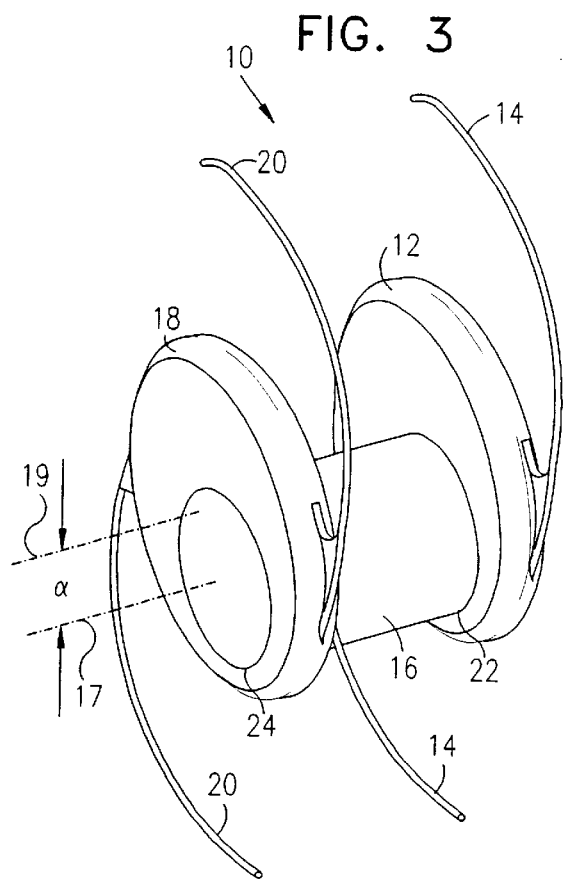
FIG. 3 is a simplified pictorial illustration of an intraocular lens implant similar to the implant of FIG. 1, except that the center of the telescope is attached offset to the center of the second carrying member, in accordance with a preferred embodiment of the present invention.

Alternatively, as shown in FIG. 3, a longitudinal axis 17 of telescope 16 may be offset a distance a (linear or angular) from a longitudinal axis 19 of carrying members 12 and 18. Alternatively, telescope 16 may be offset from just one of the carrying members 12 and 18. By offsetting telescope 16, the orientation of implant 10 may be adjusted in the eye of a patient by appropriate turning of carrying members 12 and/or 18.

Figure 2:
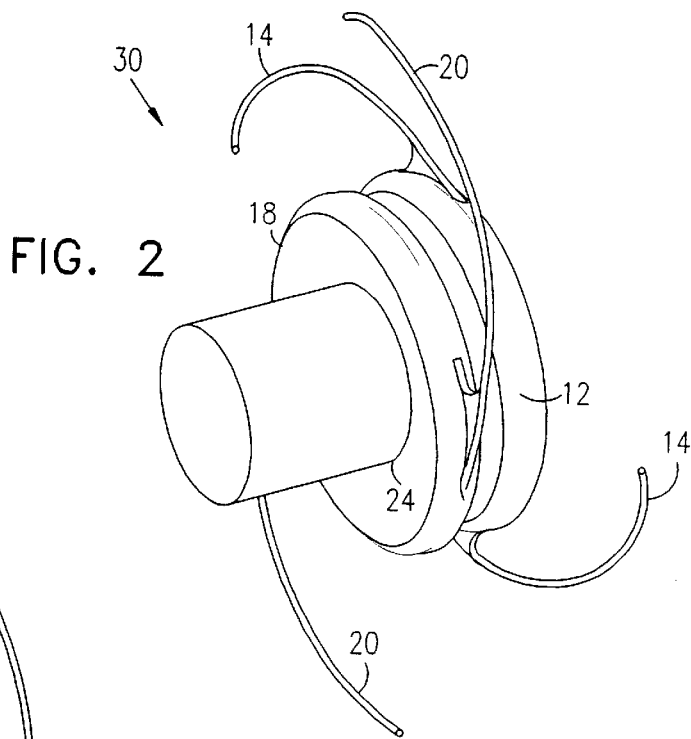
FIG. 2 is a simplified pictorial illustration of an intraocular lens implant comprising a first carrying member attached to an end of a telescope and a second carrying member attached to the telescope intermediate opposite ends of the telescope, constructed and operative in accordance with a preferred embodiment of the present invention.

Reference is now made to FIG. 2 which illustrates an intraocular lens implant 30 constructed and operative in accordance with another preferred embodiment of the present invention. Implant 30 is preferably substantially identical to implant 10, except that the at least one second carrying member 18 is attached to telescope 16 intermediate the opposite ends of telescope 16. It is appreciated that carrying members 12 and 18 may be attached at any other arbitrary positions along the telescope body.

By supporting telescope 16 by carrying members 12 and 18, any vibration or undesired displacement of telescope 16 is reduced or eliminated. The choice of placement of second carrying member 18 as shown in FIG. 1 or FIG. 2 is determined, inter alia, by the type of treatment desired and internal structure of the eye of the particular patient.

Figure 4:
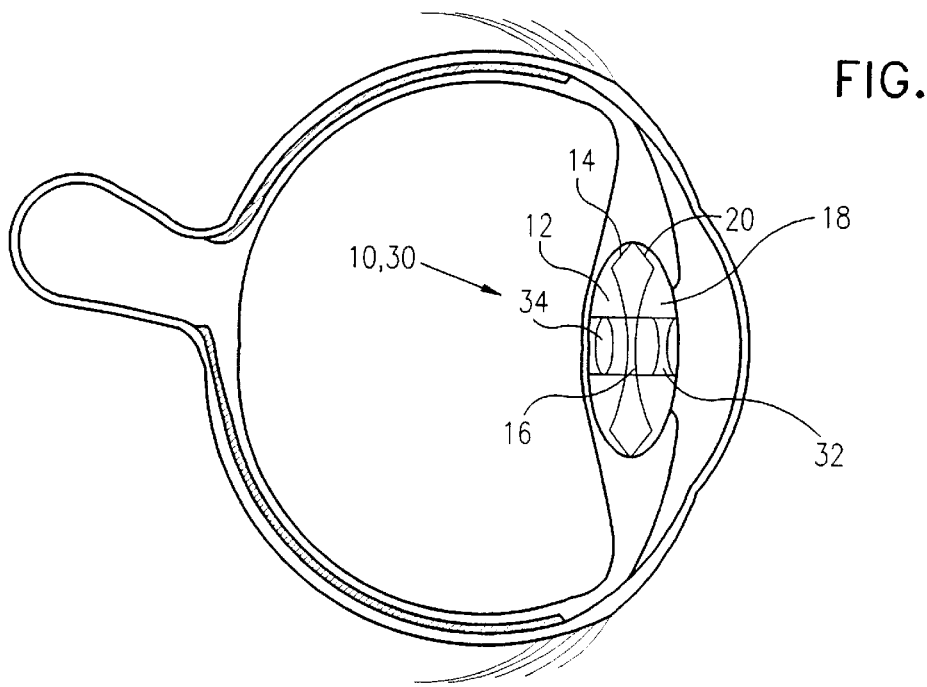
FIG. 4 is a simplified pictorial illustration of the intraocular lens implant of FIG. 1 or FIG. 2 installed in a capsular bag of an eye, the telescope not projecting into the anterior chamber, in accordance with a preferred embodiment of the present invention.

Reference is now made to FIG. 4 which illustrates intraocular lens implant 10 or 30 installed in a capsular bag of an eye. It is seen that telescope 16 does not project into the anterior chamber. The natural lens has been removed, and first carrying member 12 is attached to a distal portion of the posterior chamber and second carrying member 18 is attached to a proximal portion of the posterior chamber. Telescope 16 is shown having an anteriorly positioned negative lens 32 and a posteriorly positioned positive lens 34, thus forming a reverse Galilean telescope. It is appreciated that this is just one example of the type of telescope which may be employed, and other types may be used as well.

Figure 5:
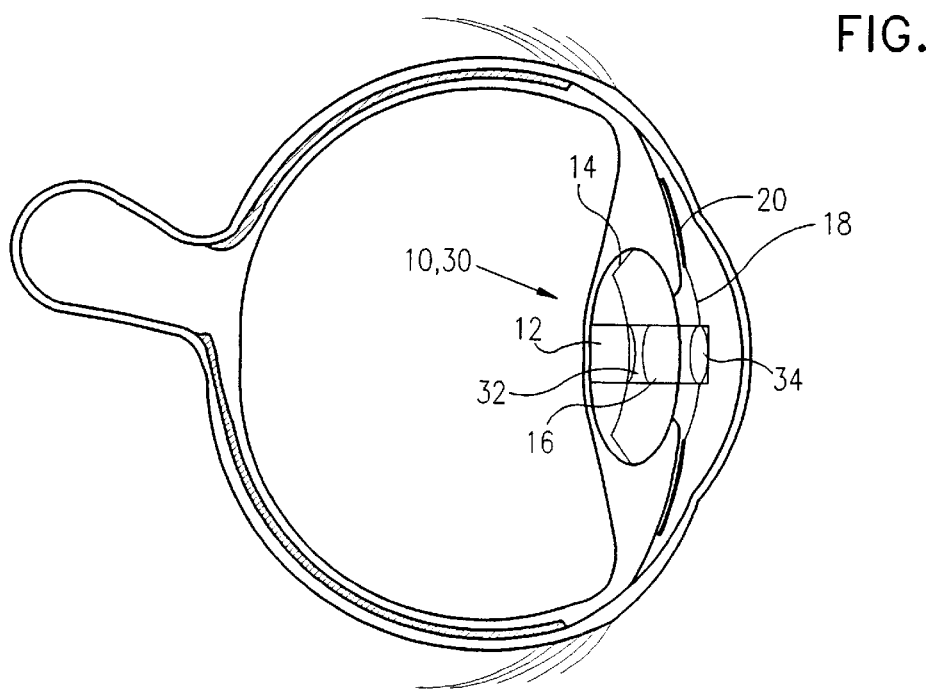
FIG. 5 is a simplified pictorial illustration of the intraocular lens implant of FIG. 1 or FIG. 2 installed in a capsular bag of an eye, the telescope projecting into the anterior chamber, in accordance with another preferred embodiment of the present invention.

Reference is now made to FIG. 5 which illustrates intraocular lens implant 10 or installed in the capsular bag. It is seen that in this embodiment, telescope 16 projects into the anterior chamber. The natural lens has been removed, and first carrying member 12 is attached to a distal portion of the posterior chamber and second carrying member 18 may be attached to a distal portion of the anterior chamber, such as the sulcus, preferably not touching the cornea or the pupil. Alternatively, second carrying member 18 may be attached to any other portion of the posterior or anterior chamber. Telescope 16 is shown with positive lens 34 anteriorly positioned and with negative lens 32 posteriorly positioned, thus forming a Galilean telescope. Again it is appreciated that this is just one example of the type of telescope which may be employed, and other types may be used as well.

Figure 6:
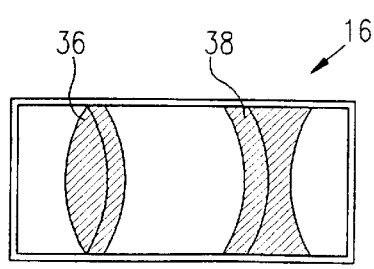
FIG. 6 is a simplified sectional illustration of the telescope of the intraocular lens implant of FIG. 1 or FIG. 2 with doublet lenses, constructed and operative in accordance with a referred embodiment of the present invention.

Reference is now made to FIG. 6 which illustrates one construction of telescope 16 in accordance with a preferred embodiment of the present invention. Telescope 16 may employ positive doublet lenses 36 and negative doublet lenses 38 to avoid chromatic aberrations. It is appreciated that in accordance with the present invention, one or more of the lenses may have a graded index of refraction, or may be holographic (diffusing).

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. An intraocular lens (IOL) implant for implantation in an eye having a capsular bag, a posterior chamber and an anterior chamber, the implant comprising:

a first carrying member adapted to be attached to said capsular bag; and a telescope attached to and extending from said first carrying member;

characterized by said telescope being further attached to at least one second carrying member, wherein said at least one second carrying member is adapted to be attached to a portion of the eye.

2. The implant according to claim 1 wherein said first carrying member is attached to an end of said telescope and said at least one second carrying member is attached to an opposite end of said telescope.

3. The implant according to claim 1 wherein said first carrying member is attached to an end of said telescope and said at least one second carrying member is attached to said telescope intermediate said end and an opposite end of said telescope.

4. The implant according to claim 1 wherein said at least one second carrying member is adapted to be attached to a portion of the posterior chamber.

5. The implant according to claim 1 wherein said telescope is adapted to extend through at least a portion of the capsular bag into the anterior chamber and said at least one second carrying member is adapted to be attached to a portion of the anterior chamber.

6. The implant according to claim 1 and wherein said first and said at least one second carrying members each comprise at least one haptic extending therefrom for attachment to a portion of said eye.

7. The implant according to claim 1 and wherein said first and said at least one second carrying members each have a bore formed therein and wherein said telescope is fixedly received in said bores.

8. The implant according to claim 7 and wherein said bores are generally circular.

9. The implant according to claim 7 and wherein a center of each said bore is generally concentric with a center of the corresponding carrying member.

10. The implant according to claim 7 and wherein a longitudinal axis of said telescope is offset from a longitudinal axis of at least one of said first and said second carrying members.

11. The implant according to claim 1 and wherein said telescope comprises an anteriorly positioned positive lens and a posteriorly positioned negative lens.

12. The implant according to claim 1 and wherein said telescope comprises an anteriorly positioned negative lens and a posteriorly positioned positive lens.

13. The implant according to claim 1 and wherein said telescope comprises lenses having a graded index of refraction.

14. The implant according to claim 1 and wherein said telescope comprises at least one holographic lens.

15. The implant according to claim 1 and wherein said telescope comprises at least one doublet lens.

* * * * *